US011452788B2

(12) United States Patent
Shin et al.

(10) Patent No.: US 11,452,788 B2
(45) Date of Patent: Sep. 27, 2022

(54) APPARATUS AND METHOD FOR STERILIZING FINGERPRINT RECOGNITION AREA

(71) Applicant: SUPREMA INC., Gyeonggi-do (KR)

(72) Inventors: Dong-mok Shin, Gyeonggi-do (KR); Myung-chul Lee, Gyeonggi-do (KR); Eun-young Jee, Gyeonggi-do (KR)

(73) Assignee: SUPREMA INC., Gyeonggi-do (KR)

( * ) Notice: Subject to any disclaimer, the term of this patent is extended or adjusted under 35 U.S.C. 154(b) by 0 days.

(21) Appl. No.: 17/105,882

(22) Filed: Nov. 27, 2020

(65) Prior Publication Data
US 2021/0361788 A1 Nov. 25, 2021

(30) Foreign Application Priority Data

May 20, 2020 (KR) .................. 10-2020-0060551
Jun. 25, 2020 (KR) .................. 10-2020-0077971

(51) Int. Cl.
A61L 2/10 (2006.01)
A61L 2/08 (2006.01)
A61L 2/24 (2006.01)
A61L 2/28 (2006.01)
G06V 40/13 (2022.01)
G06V 40/12 (2022.01)

(52) U.S. Cl.
CPC .............. *A61L 2/08* (2013.01); *A61L 2/10* (2013.01); *A61L 2/24* (2013.01); *A61L 2/28* (2013.01); *G06V 40/1318* (2022.01); *G06V 40/1365* (2022.01)

(58) Field of Classification Search
CPC ...... A61L 2/08; A61L 2/10; A61L 2/24; A61L 2/28; G06K 9/0004; G06V 40/1318
See application file for complete search history.

(56) References Cited

U.S. PATENT DOCUMENTS

| 10,918,750 | B2* | 2/2021 | Cole | A61N 5/0624 |
| 2008/0187190 | A1* | 8/2008 | Shin | A61L 2/10 |
| | | | | 422/24 |
| 2012/0126134 | A1* | 5/2012 | Deal | G01J 1/429 |
| | | | | 250/372 |
| 2016/0296650 | A1* | 10/2016 | Liao | A61L 2/10 |
| 2017/0032166 | A1* | 2/2017 | Raguin | G06V 40/13 |
| 2019/0091358 | A1* | 3/2019 | Liao | H05B 45/10 |
| 2020/0268921 | A1* | 8/2020 | Lepine | A61L 2/08 |
| 2020/0390922 | A1* | 12/2020 | Stibich | A61L 2/10 |
| 2021/0052757 | A1* | 2/2021 | Baarman | G16H 10/60 |

* cited by examiner

*Primary Examiner* — Wyatt A Stoffa
(74) *Attorney, Agent, or Firm* — Maier & Maier, PLLC

(57) ABSTRACT

An apparatus for sterilizing a fingerprint recognition area, the apparatus includes at least one finger contact unit for obtaining a fingerprint image on which a body of a user is contacted, a sterilizing light emitting unit configured to emit the sterilizing light onto the at least one finger contact unit for obtaining the fingerprint image, at least one optical sensing unit configured to sense the sterilizing light emitted onto the at least one finger contact unit for obtaining the fingerprint image and a control unit configured to determine an ON timing of the sterilizing light emitting unit after performing user authentication for the user, and determine an OFF timing of the sterilizing light emitting unit based on a result of comparing an accumulated value of the calculated energy of the sterilizing light with a predetermined reference energy.

21 Claims, 7 Drawing Sheets

APPARATUS AND METHOD FOR STERILIZING FINGERPRINT RECOGNITION AREA

CROSS-REFERENCE TO RELATED APPLICATIONS

This application is based on and claims priorities from Korean Patent Application Nos. 10-2020-0060551, 10-2020-0077971, respectively filed on May 20, 2020 and Jun. 25, 2020, the disclosures of which are incorporated herein in their entireties by reference for all purposes.

TECHNICAL FIELD

The present disclosure relates to an apparatus and a method for sterilizing a fingerprint recognition area.

BACKGROUND

A device (or an apparatus) that requires contact with a user, such as a fingerprint acquisition apparatus, is very likely to spread a large number of pathogens because a plurality of users use their fingers to touch the fingerprint recognition area when acquiring fingerprints.

A number of the pathogens show a feature that the pathogens are effectively inactivated when exposed to high-energy illumination, such as ultraviolet rays (UV). Since a sterilizing effect is obtained through the feature, to prevent the spread of the pathogens on the device such as the current fingerprint acquisition apparatus, a method of obtaining the sterilizing effect on the fingerprint recognition area by using the high-energy illumination is being considered.

However, the high-energy illumination such as the ultraviolet rays (UV) can have a harmful effect on the human body, and an existing problem is that minimum energy for achieving the sterilizing effect for each of a plurality of the pathogens varies depending on a type of pathogens.

SUMMARY

The present disclosure provides an apparatus and a method for sterilizing a fingerprint recognition area.

In addition, the present disclosure may provide the apparatus for sterilizing the fingerprint recognition area that emits sterilizing light onto an area on which a body of a user is contacted, calculates energy of the emitted sterilizing light, and controls the sterilizing light not to be emitted onto the area on which the body of the user is contacted if an accumulated amount of the calculated energy approaches predetermined reference energy.

In accordance with an aspect of the present disclosure, there is provided an apparatus for sterilizing a fingerprint recognition area, the apparatus comprising: at least one finger contact unit for obtaining a fingerprint image on which a body of a user is contacted; a sterilizing light emitting unit configured to emit the sterilizing light onto the at least one finger contact unit for obtaining the fingerprint image; at least one optical sensing unit configured to sense the sterilizing light emitted onto the at least one finger contact unit for obtaining the fingerprint image; and a control unit configured to determine an ON timing of the sterilizing light emitting unit after performing user authentication for the user, calculate energy of the sterilizing light based on the sterilizing light sensed by the at least one optical sensing unit from the ON timing of the sterilizing light emitting unit, and determine an OFF timing of the sterilizing light emitting unit based on a result of comparing an accumulated value of the calculated energy of the sterilizing light with a predetermined reference energy.

The apparatus for sterilizing a fingerprint recognition area further comprises an imaging device configured to capture the fingerprint image of a finger of the user contacted on the at least one finger contact unit for obtaining the fingerprint image, wherein the control unit is configured to perform the user authentication based on the fingerprint image of the user captured by the imaging device.

The at least one optical sensing unit is further configured to output a current or a voltage corresponding to the sensed sterilizing light, and wherein the control unit is configured to calculate the energy of the sterilizing light by using the current or the voltage output from the at least one optical sensing unit.

The control unit is further configured to control the sterilizing emitting unit to be off if the accumulated value of the energy is equal to or greater than the predetermined reference energy.

The sterilizing light includes infrared rays or ultraviolet rays.

The at least one optical sensing unit comprises: a first optical sensing unit configured to sense a direct Light emitted from the sterilizing light emitting unit; a second optical sensing unit configured to sense a first reflected light that the sterilizing light, which is emitted from the sterilizing light emitting unit, is reflected by the at least one finger contact unit for obtaining the fingerprint image; a third optical sensing unit configured to sense a second reflected light that the sterilizing light, which is emitted from the sterilizing light emitting unit, is reflected by the body of the user or an object; and a fourth optical sensing unit configured to sense a transmitted light that the sterilizing light, which is emitted from the sterilizing light emitting unit, is transmitted through the at least one finger contact unit for obtaining the fingerprint image.

The control unit is further configured to determine a time at which at least one of the direct light, the first reflected light, and the transmitted light is not sensed by the first optical sensing unit, the second optical sensing unit, and the fourth optical sensing unit respectively or at which the second reflected light is sensed by the third optical sensing unit as a body contact start time at which contact with the body of the user is occurred on the at least one finger contact unit for obtaining the fingerprint image; and determine a time, after determining that the contact with the body of the user is occurred, at which the direct light, the first reflected light, and the transmitted light are sensed by the first optical sensing unit, the second optical sensing unit, and the fourth optical sensing unit respectively or at which the second reflected light is not sensed by the third optical sensing unit as a body contact end time at which the contact with the body is terminated.

The control unit is further configured to determine a time at which a sensing state of at least one of the direct light, the first reflected light, the second reflected light, and the transmitted light of the sterilizing light is changed in the at least one optical sensing unit as a body contact start time at which contact with the body of the user is occurred on the at least one finger contact unit for obtaining the fingerprint image; and determine a time, after determining that the contact with the body of the user is occurred, at which the sensing state of at least one of the direct light, the first reflected light, the second reflected light, and the transmitted light of the sterilizing light is changed in the at least one optical sensing unit as a body contact end time at which the contact with the body is terminated.

The control unit is further configured to reset the predetermined reference energy based on a time in which the contact with the body of the user has maintained from the body contact start time to the body contact end time.

The control unit is further configured to reset the predetermined reference energy based on the number of times determined that the contact with the body of the user has been occurred on the at least one finger contact unit for obtaining the fingerprint image.

The control unit is further configured to reset the predetermined reference energy based on a calculated contamination level of the at least one finger contact unit for obtaining the fingerprint image.

The contamination level calculated by the control unit is calculated based on a comparison between a reference image showing the at least one finger contact unit for obtaining the fingerprint image in an initial state in which the body of the user has not been contacted on the at least one finger contact unit for obtaining the fingerprint image and a captured image showing the at least one finger contact unit for obtaining the fingerprint image after the body of the user is inserted into the apparatus for sterilizing the fingerprint recognition area and contacted on the at least one finger contact unit for obtaining the fingerprint image, and after the user authentication is terminated.

The contamination level calculated by the control unit is calculated based on a change in contrast between the reference image and the captured image.

The control unit is further configured to obtain an area ratio of the body of the user contacted on the at least one finger contact unit for obtaining the fingerprint image to the at least one finger contact unit for obtaining the fingerprint image in an image showing the at least one finger contact unit for obtaining the fingerprint image in a state in which the body of the user is inserted and contacted on the at least one finger contact unit for obtaining the fingerprint image.

The control unit is further configured to reset the predetermined reference energy based on calculated transparency of the at least one finger contact unit for obtaining the fingerprint image, and the transparency is calculated based on a comparison of an amount of a light sensed by an optical sensing unit sensing a direct light of the sterilizing light emitted from the sterilizing light emitting unit to those sensed by an optical sensing unit sensing a transmitted light that the sterilizing light emitted from the sterilizing light emitting unit is transmitted through the at least one finger contact unit for obtaining the fingerprint image.

The apparatus for sterilizing a fingerprint recognition area further comprises temperature sensor or a humidity sensor, wherein the control unit is further configured to reset the predetermined reference energy based on sensed temperature and sensed humidity.

The apparatus for sterilizing a fingerprint recognition area further comprises a temperature sensor or a humidity sensor, wherein the control unit is further configured to adjust output intensity of the sterilizing light emitting unit based on sensed temperature and sensed humidity.

The control unit is further configured to determine that the sterilizing light emitting unit is deteriorated if the sterilizing light sensed through the at least one optical sensing unit is out of a predetermined intensity range of the sterilizing light.

The control unit is further configured to output information including a message indicating that an abnormality has occurred in the sterilizing light emitting unit if the control unit determines that the sterilizing light emitting unit is deteriorated.

The apparatus for sterilizing a fingerprint recognition area further comprises at least one illuminant configured to generate, if a sterilizing light having a first wavelength is emitted from the sterilizing light emitting unit onto the at least one illuminant, a reflected light having a second wavelength different from the first wavelength, wherein the first wavelength is in a wavelength range of infrared rays or ultraviolet rays, and the second wavelength is in a wavelength range of visible light.

The apparatus for sterilizing a fingerprint recognition area further comprises an optical sensing unit, positioned under the at least one finger contact unit for obtaining the fingerprint image, configured to sense the reflected light having the second wavelength generated from the at least one illuminant.

The apparatus for sterilizing a fingerprint recognition area further comprises an imaging sensor configured to output an electrical signal corresponding to the second wavelength by sensing the reflected light generated from the at least one illuminant.

In accordance with another aspect of the present disclosure, there is provided a method of sterilizing a fingerprint recognition area performed by an apparatus for sterilizing the fingerprint recognition area, the method comprising: emitting a sterilizing light onto at least one finger contact unit for obtaining a fingerprint image on which a body of a user is contacted by using a sterilizing light emitting unit; sensing the sterilizing light emitted onto the at least one finger contact unit for obtaining the fingerprint image; and determining an ON timing of the sterilizing light emitting unit after performing user authentication for the user, calculating energy of the sterilizing light based on the sensed sterilizing light from the ON timing of the sterilizing light emitting unit, and determining an OFF timing of the sterilizing light emitting unit based on a result of comparing an accumulated value of the calculated energy of the sterilizing light with a predetermined reference energy.

According to one embodiment, the apparatus for sterilizing the fingerprint recognition area may determine an ON timing (which may be a timing to emit the sterilizing light) of a sterilizing light emitting unit after performing user authentication for the user, calculate the energy of the sterilizing light based on the sterilizing light sensed by an optical sensing unit from the ON timing of the sterilizing light emitting unit, and determine an OFF timing (which may be a timing not to emit the sterilizing light) of the sterilizing light emitting unit based on a result of a comparison between an accumulated value of the calculated energy of the sterilizing light and the predetermined reference energy.

In addition, since the predetermined reference energy may be reset according to a time determined in which the body of the user has been contacted on the finger contact area for obtaining a fingerprint image, the number of times determined that the body of the user has been contacted, a contamination level, transparency, temperature and humidity, a sterilization effect may be obtained by resetting the reference energy determined to have the sterilization effect according to changes in a surrounding environment.

DETAILED DESCRIPTION

The advantages and features of exemplary embodiments of the present disclosure and methods of accomplishing them will be clearly understood from the following description of the embodiments taken in conjunction with the accompanying drawings. However, the present disclosure is not limited to those embodiments and is implemented in various forms. It is noted that the embodiments are provided to make a full disclosure and also to allow those skilled in the art to know the full scope of the present disclosure.

In the following description, well-known functions and/or configurations will not be described in detail if they would unnecessarily obscure the features of the disclosure. Further, the terms to be described below are defined in consideration of their functions in the embodiments of the disclosure and vary depending on a user's or operator's intention or practice. Accordingly, the definition is made on a basis of the content throughout the present disclosure.

Figure 1:
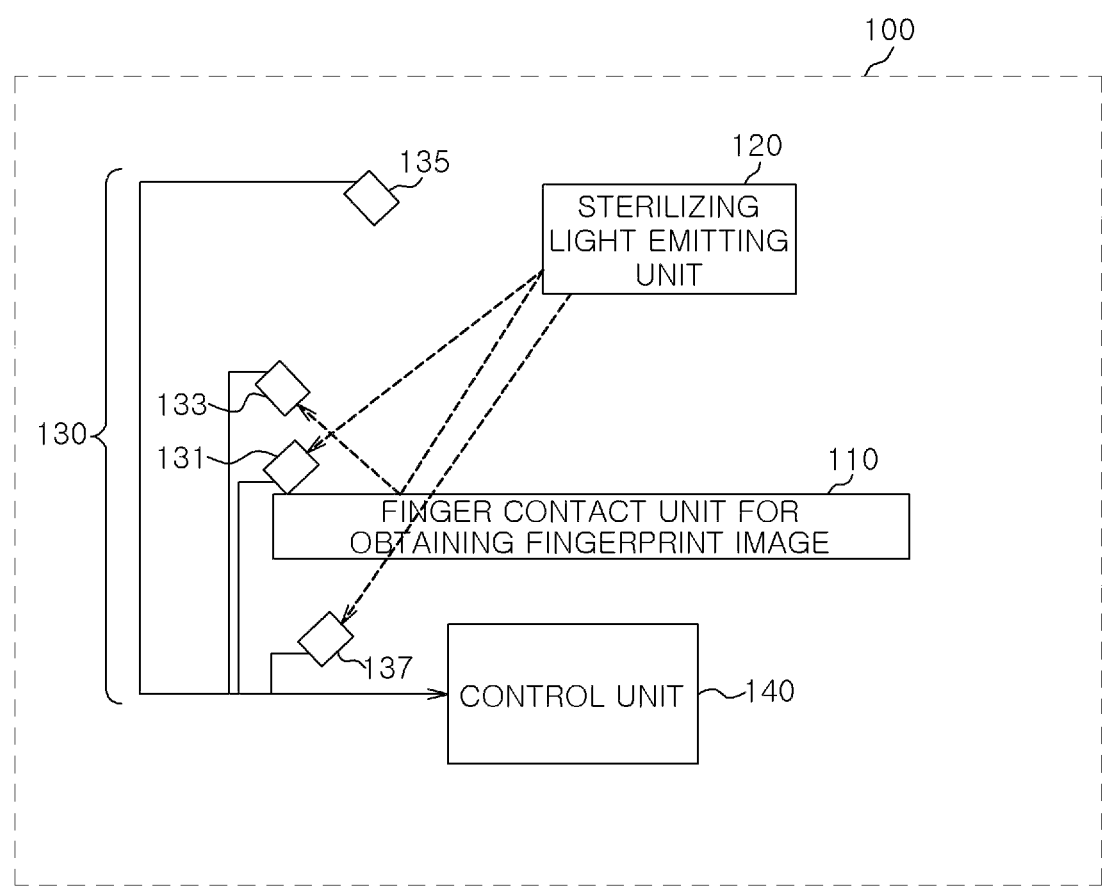
FIG. 1 shows a configuration of an apparatus for sterilizing a fingerprint recognition area according to one embodiment.

FIG. 1 shows a configuration of an apparatus 100 for sterilizing a fingerprint recognition area according to one embodiment.

Referring to FIG. 1, the apparatus 100 for sterilizing the fingerprint recognition area according to one embodiment may include a finger contact unit 110 for obtaining a fingerprint image, a sterilizing light emitting unit 120, an optical sensing unit 130, and a control unit 140, but is not limited to those described above. In addition, each of the apparatus 100 for sterilizing the fingerprint recognition area and components included therein may be implemented in a form of a software module or a hardware module, or may be implemented in a combination of the software module and the hardware module, for example, a computer or a smart device or the like, and each of the components may be electrically connected.

The finger contact unit 110 for obtaining the fingerprint image may be an area on which a body of a user (for example, the finger of the user) is contacted. In other words, the user may put his/her finger on the finger contact unit 110 for obtaining the fingerprint image.

For example, the finger contact unit 110 for obtaining the fingerprint image may be a scanner capable of scanning the body of the user (for example, the finger of the user). The finger contact unit 110 for obtaining the fingerprint image may be an optical scanner or another type of the scanner such as a capacitance scanner, an ultrasound fingerprint scanner, or a thermal scanner.

There may be a plurality of the finger contact unit 110 for obtaining the fingerprint image, for example, the finger contact unit 110 for obtaining the fingerprint image may include a first finger contact unit for obtaining the fingerprint image and a second finger contact unit for obtaining the fingerprint image.

The first finger contact unit for obtaining the fingerprint image and the second finger contact unit for obtaining the fingerprint image may be controlled by the control unit 140 to be slid so that the first finger contact unit for obtaining the fingerprint image and the second finger contact unit for obtaining the fingerprint image may be selectively used by the user.

The sterilizing light emitting unit 120 may be controlled by the control unit 140 to emit the sterilizing light onto at least one finger contact unit 110 for obtaining the fingerprint image. In addition, the sterilizing light emitting unit 120 may be connected to the control unit 140 by wire or wireless.

For example, the sterilizing light emitting unit 120 may include a sterilizing light source (not shown), and may emit the sterilizing light onto the finger contact unit 110 for obtaining the fingerprint image by using the sterilizing light source controlled by the control unit 140.

The sterilizing light emitting unit 120 may emit the sterilizing light onto an area including a side portion (or an edge portion) and a central portion of the finger contact unit 110 for obtaining the fingerprint image under the control of the control unit 140.

Herein, the sterilizing light may be at least one of infrared rays and ultraviolet rays (UV) with a wavelength range having a sterilization function, but is not limited thereto.

The optical sensing unit 130 may sense the sterilizing light emitted onto the finger contact unit 110 for obtaining the fingerprint image, and may output a current or a voltage corresponding to the sensed sterilizing light. In addition, the optical sensing unit 130 may measure illuminance of the sterilizing light emitted onto the finger contact unit 110 for obtaining the fingerprint image, and may output a current or a voltage corresponding to the measured illuminance of the sterilizing light, but is not limited thereto.

The optical sensing unit 130 may transmit the output current or the output voltage to the control unit 140. In addition, the optical sensing unit 130 may be connected to the control unit 140 by wire or wireless.

The optical sensing unit 130 may be positioned within a predetermined distance from the finger contact unit 110 for obtaining the fingerprint image. For example, the optical sensing unit 130 may be positioned at the side portion (or the edge portion) of the finger contact unit 110 for obtaining the fingerprint image.

According to one embodiment, the optical sensing unit 130 may include at least one of a first optical sensing unit 131, a second optical sensing unit 133, a third optical sensing unit 135 and a fourth optical sensing unit 137. Each of the first optical sensing unit 131, the second optical sensing unit 133, the third optical sensing unit 135 and the fourth optical sensing unit 137 may sense the sterilizing light emitted onto the finger contact unit 110 for obtaining the fingerprint image, and if two or more of the first optical sensing unit 131, the second optical sensing unit 133, the third optical sensing unit 135 and the fourth optical sensing unit 137 are provided, the sterilizing light emitted onto the finger contact unit 110 for obtaining the fingerprint image may be sensed more accurately. However, the above description is not limited thereto, and the optical sensing unit 130 may include an optical sensing unit other than the first optical sensing unit 131, the second optical sensing unit 133, the third optical sensing unit 135, and the fourth optical sensing unit 137, for example, a separate optical sensing unit having two or more functions of the first optical sensing unit 131 through the fourth optical sensing unit 137.

For example, a single optical sensing unit may play a role of the first optical sensing unit 131 for sensing the sterilizing light emitted from the sterilizing light emitting unit 120 and a role of the second optical sensing unit 133 for sensing a first reflected light that is the sterilizing light emitted from the sterilizing light emitting unit 120 and then reflected by the finger contact unit 110 for obtaining the fingerprint image together.

The first optical sensing unit 131 may sense a direct light of the sterilizing light directly emitted from the sterilizing light emitting unit 120 onto the finger contact unit 110 for obtaining the fingerprint image, thereby outputting a current or a voltage.

The second optical sensing unit 133 may sense the first reflected light that is the sterilizing light emitted from the sterilizing light emitting unit 120 and then reflected by the finger contact unit 110 for obtaining the fingerprint image, thereby outputting a current or a voltage.

The third optical sensing unit 135 may sense a second reflected light that is the sterilizing light emitted from the sterilizing light emitting unit 120 and then reflected by the body of the user (for example, the finger of the user) or an object, thereby outputting a current or a voltage.

For example, the third optical sensing unit 135 may be positioned within a predetermined distance from the sterilizing light emitting unit 120, and thus, the third optical sensing unit 135 may sense the sterilizing light when a user's finger is proceeding toward the finger contact unit 110 for obtaining the fingerprint image. Afterwards, the sterilizing light may not be sensed by the optical sensing units 131, 133, and 137 when the user's finger is positioned in a light path from the sterilizing light emitting unit 120 to the optical sensing units 131, 133, and 137 to thereby completely blocks or reflects the sterilizing light emitted from the sterilizing light emitting unit 120 and directly reaching the optical sensing units 131, 133, and 137.

The fourth optical sensing unit 137 may sense a transmitted light that is the sterilizing light emitted from the sterilizing light emitting unit 120 and then transmitted through the finger contact unit 110 for obtaining the fingerprint image, thereby outputting a current or a voltage.

The control unit 140 may receive the current or the voltage output from the optical sensing unit 130, and may calculate an output value of the sterilizing light based on the current or the voltage output received from the optical sensing unit 130.

For example, the control unit 140 may calculate the output value of the sterilizing through Equation 1 below.

$$P_o(t) = K_i I_s(t) \quad \text{[Equation 1]}$$
$$= K_v V_s(t)$$

Herein, $P_o(t)$ is an output value of the sterilizing light, $K_i$ and $K_v$ are constants, $I_s(t)$ is a current value corresponding to the output of the sterilizing light, and $V_s(t)$ is a voltage value corresponding to the output of the sterilizing light. In addition, the current value $I_s(t)$ is proportional to the output value of the sterilizing light $P_o(t)$ and the voltage value $V_s(t)$ is proportional to the output value of the sterilizing light $P_o(t)$.

After performing user authentication for the user, the control unit 140 may determine an ON timing (which may be a timing at which the sterilizing light emitting unit 120 starts emitting the sterilizing light) of the sterilizing light emitting unit 120, and may calculate energy of the sterilizing light based on the sterilizing light sensed by the optical sensing unit 130, an accumulated value of the calculated energy of the sterilizing light from the ON timing of the sterilizing light emitting unit 120 based on the output value. The control unit 140 may determine an OFF timing (which may be a timing at which the sterilizing light emitting unit 120 stops emitting the sterilizing light) of the sterilizing light emitting unit 120 based on a result of a comparison between the accumulated value of the calculated energy of the sterilizing light and a predetermined reference energy.

For example, the control unit 140 may calculate the accumulated value of the calculated energy of the sterilizing light through Equation 2 below.

$$E_o(t) = \int_0^t P_o(\tau)d\tau \quad \text{[Equation 2]}$$
$$= K_i \int_0^t I_s(\tau)d\tau$$
$$= K_v \int_0^t V_s(\tau)d\tau$$

Herein, $E_o(t)$ indicates the accumulated value of the energy of the sterilizing light.

In a different way, the control unit 140 may calculate an accumulated value of the current corresponding to the sterilizing light, and the accumulated value of the energy of the sterilizing light based on the accumulated value of the current. In addition, the control unit 140 may determine the OFF timing (which may be the timing at which the sterilizing light emitting unit 120 stops emitting the sterilizing light) of the sterilizing light emitting unit 120 based on the comparison between the accumulated value of the energy of the sterilizing light and the predetermined reference energy. The control unit 140 may control the sterilizing emitting unit to be off if the accumulated value of the energy is equal to or greater than the predetermined reference energy.

For example, the control unit 140 may calculate the accumulated value of the energy of the sterilizing light through Equation 3 below.

In this case, the control unit 140 may measure a change in a voltage of a capacitor (not shown) by accumulating the current output from the optical sensing unit 130 by using the capacitor, but is not limited thereto.

$$\Delta V_c(t) = \frac{1}{c}\int_0^t I_s(\tau)d\tau \quad \text{[Equation 3]}$$
$$\int_0^t I_s(\tau)d\tau = C\Delta V_c(t)$$
$$E_o(t) = K_i \int_0^t I_s(\tau)d\tau = CK_i\Delta V_c(t)$$

Herein, $\Delta V_c(t)$ is a value of the change in the voltage for the accumulated current corresponding to the sterilizing light, and C is a constant.

The control unit 140 may determine a time at which a sensing state of at least one of the direct light, the first reflected light, the second reflected light, and the transmitted light of the sterilizing light is changed in the at least one optical sensing unit 130 as a body contact start time at which contact with the body of the user is occurred on the at least one finger contact unit 110 for obtaining the fingerprint image. After determining that the contact with the body of the user is occurred, the control unit 140 may determine a time at which the sensing state of at least one of the direct light, the first reflected light, the second reflected light, and the transmitted light of the sterilizing light is changed as a body contact end time at which the contact with the body of the user is terminated.

Herein, the change in the sensing state of the sterilizing light in the at least one optical sensing unit 130 may indicate that the direct light, the first reflected light, and the transmitted light of the sterilizing light that have been sensed begin not to be sensed, or the second reflected light of the sterilizing light that has not been sensed begins to be sensed. In addition, when the sensing state of the sterilizing light in the at least one optical sensing unit 130 is changed again may indicate that the direct light, the first reflected light, and the transmitted light of the sterilizing light that began not to be sensed begin to be sensed, or the second reflected light of the sterilizing light that began to be sensed begins not to be sensed.

For example, the control unit 140 may determine a time at which at least one of the direct light, the first reflected light, and the transmitted light begins not to be sensed by the first optical sensing unit 131, the second optical sensing unit 133, and the fourth optical sensing unit 137 respectively, or a time at which the second reflected light begins to be sensed by the third optical sensing unit 135 as the body contact start time at which the contact with the body of the user (for example, the finger of the user) is occurred on the finger contact unit 110 for obtaining the fingerprint image. After determining that the contact with the body of the user is occurred, the control unit 140 may determine a time at which the direct light, the first reflected light, and the transmitted light begin to be sensed by the first optical sensing unit 131, the second optical sensing unit 133, and the fourth optical sensing unit 137 respectively or a time at which the second reflected light begins not to be sensed by the third optical sensing unit 135 as the body contact end time at which the contact with the body of the user is terminated.

The control unit 140 may reset the predetermined reference energy based on a time in which the contact with the body of the user has maintained from the body contact start time to the body contact end time.

For example, the control unit 140 may raise the predetermined reference energy if the time in which the contact with the body of the user has maintained on the finger contact unit 110 for obtaining the fingerprint image is longer than a predetermined time. If the time in which the contact with the body of the user has maintained on the finger contact unit 110 for obtaining the fingerprint image is shorter than the predetermined time, the control unit 140 may lower the predetermined reference energy.

The control unit 140 may reset the predetermined reference energy based on the number of times determined that the contact with the body of the user has occurred on the finger contact unit 110 for obtaining the fingerprint image.

For example, if the number of times determined that the contact with the body of the user has occurred on the finger contact unit 110 for obtaining the fingerprint image is greater than a predetermined number, the control unit 140 may raise the predetermined reference energy. If the number of times determined that the contact of the body of the user has occurred on the finger contact unit 110 for obtaining the fingerprint image is smaller than the predetermined number, the control unit 140 may lower the predetermined reference energy.

The control unit 140 may reset the predetermined reference energy based on a calculation of a contamination level of the finger contact unit 110 for obtaining the fingerprint image. For example, the control unit 140 may raise the predetermined reference energy if the calculated contamination level of the finger contact unit 110 for obtaining the fingerprint image is higher than a predetermined level. If the calculated contamination level of the finger contact unit 110 for obtaining the fingerprint image is smaller than the predetermined level, the control unit 140 may lower the predetermined reference energy.

At this time, the control unit 140 may calculate the contamination level based on a comparison between a reference image showing the finger contact unit 110 for obtaining the fingerprint image in an initial state in which the body of the user has never been contacted on the finger contact unit 110 for obtaining the fingerprint image and a captured image showing the finger contact unit 110 for obtaining the fingerprint image after the body of the user contacts the finger contact unit 110 for obtaining the fingerprint image to complete the user authentication.

In addition, the control unit 140 may calculate the contamination level based on a change in contrast between the reference image and the captured image.

In addition, the control unit 140 may obtain, from the captured image showing the finger contact unit 110 for obtaining the fingerprint image, an area ratio of the body of the user contacted on the finger contact unit 110 for obtaining the fingerprint image to the finger contact unit 110 for obtaining the fingerprint image in a state in which the body of the user is inserted and contacted on the finger contact unit 110 for obtaining the fingerprint image. The control unit 140 may calculate the contamination level based on the obtained area ratio.

The control unit 140 may reset the predetermined reference energy based on a calculation of transparency of the finger contact unit 110 for obtaining the fingerprint image. For example, if the calculated transparency of the finger contact unit 110 for obtaining the fingerprint image is higher than a predetermined value, the control unit 140 may lower the predetermined reference energy. If the calculated transparency of the finger contact unit 110 for obtaining the fingerprint image is smaller than the predetermined value, the control unit 140 may raise the predetermined reference energy.

The control unit 140 may calculate the transparency based on a comparison of an amount of a light sensed by an optical sensing unit (which may be the first optical sensing unit 131) for sensing the direct light of the sterilizing light emitted from the sterilizing light emitting unit 120 to an amount of a light sensed by the fourth optical sensing unit 137 for sensing the transmitted light that is the sterilizing light emitted from the sterilizing light emitting unit 120 and then transmitted through the finger contact unit 110 for obtaining the fingerprint image.

If the sterilizing light sensed through the optical sensing unit 130 is out of a predetermined intensity range of the sterilizing light, the control unit 140 may determine that the sterilizing light emitting unit 120 is deteriorated.

If the control unit 140 determines that the sterilizing light emitting unit 120 is deteriorated, the control unit 140 may output information including a message indicating that an abnormality has occurred in the sterilizing light emitting unit 120.

When a user manipulates the apparatus 100, the control unit 140 may control the sterilizing light emitting unit 120 not to emit the sterilizing light since the user may be in danger by being exposed to the sterilizing light emitted from the deteriorated sterilizing light emitting unit 120.

For example, the apparatus 100 may further include a distance detecting sensor (not shown) configured to detect the user whether the user is positioned within a predetermined distance from the apparatus 100. When the sensor detects that the user is within the predetermined distance, the control unit 140 may control the sterilizing light emitting unit 120 which has been determined to be deteriorated not to emit the sterilizing light.

In another exemplary embodiment, if the control unit 140 recognizes the user through a user's information inputted by the user, the control unit 140 may control the sterilizing light emitting unit 120 which has been determined to be deteriorated not to emit the sterilizing light. For example, since the control unit 140 may recognize the user through the user's information including at least one of a user authentication card of the user and an ID and a password of the user without using a fingerprint for the user authentication technique, the control unit 140 may control the deteriorated sterilizing light emitting unit 120 not to emit the sterilizing light.

The control unit 140 may control the first finger contact unit for obtaining the fingerprint image and the second finger contact unit for obtaining the fingerprint image.

According to one embodiment, the apparatus 100 for sterilizing the fingerprint recognition area may further include a driving unit (not shown) capable of sliding the first finger contact unit for obtaining the fingerprint image and the second finger contact unit for obtaining the fingerprint image.

At this time, the control unit 140 may determine a time at which the first finger contact unit for obtaining the fingerprint image or the second finger contact unit for obtaining the fingerprint image is to be used for the user, and the control unit 140 may control the driving unit (not shown) according to the determined time at which the first finger contact unit for obtaining the fingerprint image or the second finger contact unit for obtaining the fingerprint image is to be used for the user. In this case, the driving unit (not shown) may slide the first finger contact unit for obtaining the fingerprint image and the second finger contact unit for obtaining the fingerprint image under the control of the control unit 140.

In more detail, the control unit 140 may determine a time after the first finger contact unit for obtaining the fingerprint image or the second finger contact unit for obtaining the fingerprint image is used or a time at which the first finger contact unit for obtaining the fingerprint image is used more than a predetermined number of times as the time at which the first finger contact unit for obtaining the fingerprint image or the second finger contact unit for obtaining the fingerprint image is to be used for the user.

Figure 2:
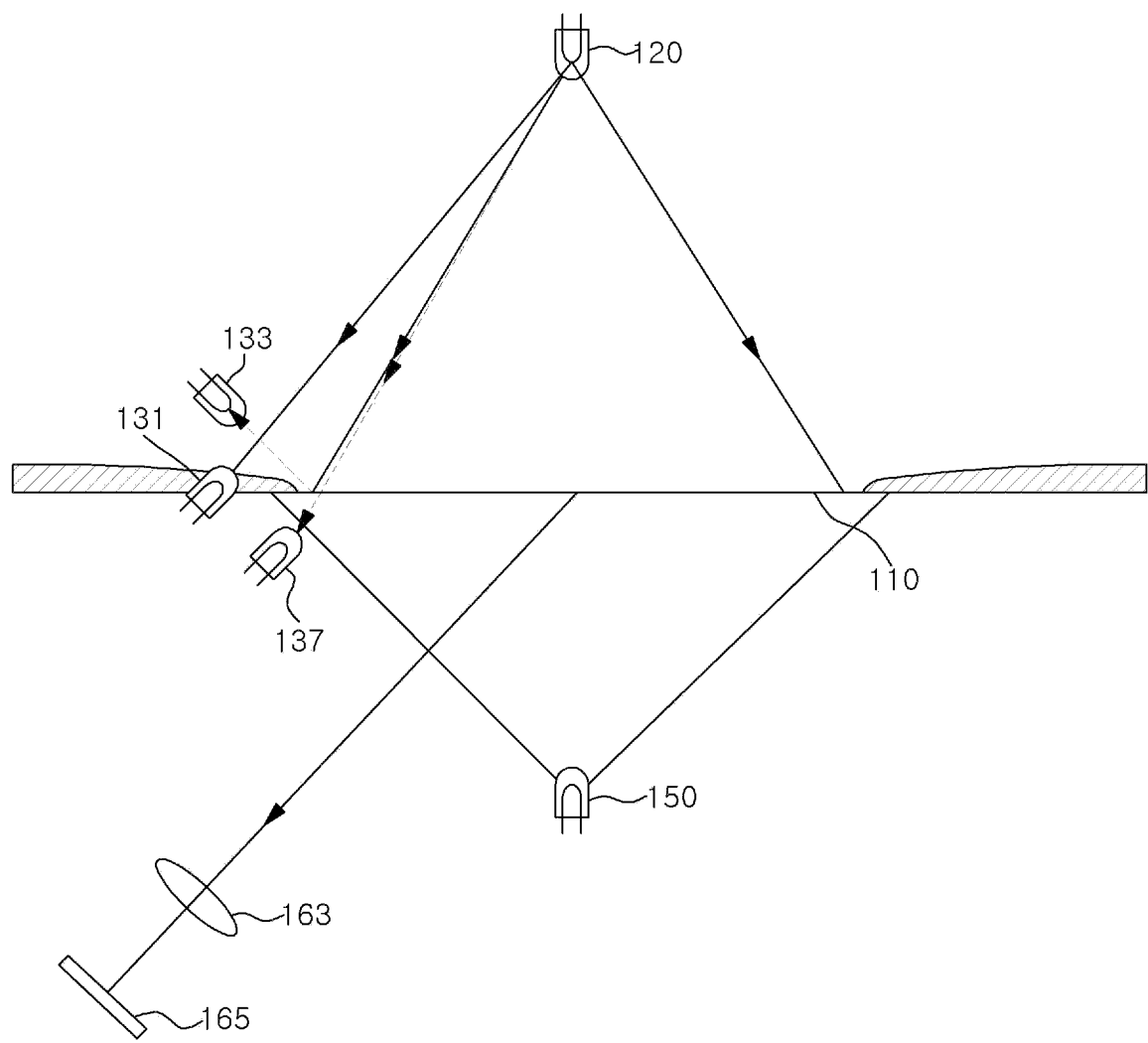
FIG. 2 shows another configuration of an apparatus for sterilizing a fingerprint recognition area according to one embodiment.

FIG. 2 shows another configuration of the apparatus 100 for sterilizing the fingerprint recognition area according to one embodiment.

Referring to FIG. 2, the apparatus 100 for sterilizing the fingerprint recognition area according to one embodiment may further include a photographic lighting device 150, a lens 163, an image sensor 165, and a signal circuit unit (not shown) under the finger contact unit 110 for obtaining the fingerprint image.

For example, the photographic lighting device 150, the lens 163, the image sensor 165, and the signal circuit unit (not shown) may be an imaging device to capture a fingerprint image of a finger of a user contacted on the finger contact unit 110 for obtaining the fingerprint image. In this case, the control unit 140 may perform user authentication based on the fingerprint image of the user captured by the imaging device.

The photographic lighting device 150 may emit an illumination (or a light) for capturing an image of a body (for example, a finger) contacted on the finger contact unit 110 for obtaining the fingerprint image.

The lens 163 may receive and pass a reflected light of the illumination (or the light) emitted from the photographic lighting device 150 to the finger contact unit 110 for obtaining the fingerprint image and then reflected by the finger contact unit 110 for obtaining the fingerprint image.

The image sensor 165 may transmit a digital signal, which is an electrical signal corresponding to the light transmitted through the lens 163, to the signal circuit unit (not shown), and the signal circuit unit (not shown) may transmit the digital signal received from the image sensor 165 to the control unit 140. At this time, the control unit 140 may obtain a biometric information of the user (for example, a fingerprint of the finger of the user) contacted on the finger contact unit 110 for obtaining the fingerprint image based on the digital signal received from the signal circuit unit (not shown).

Figure 3:
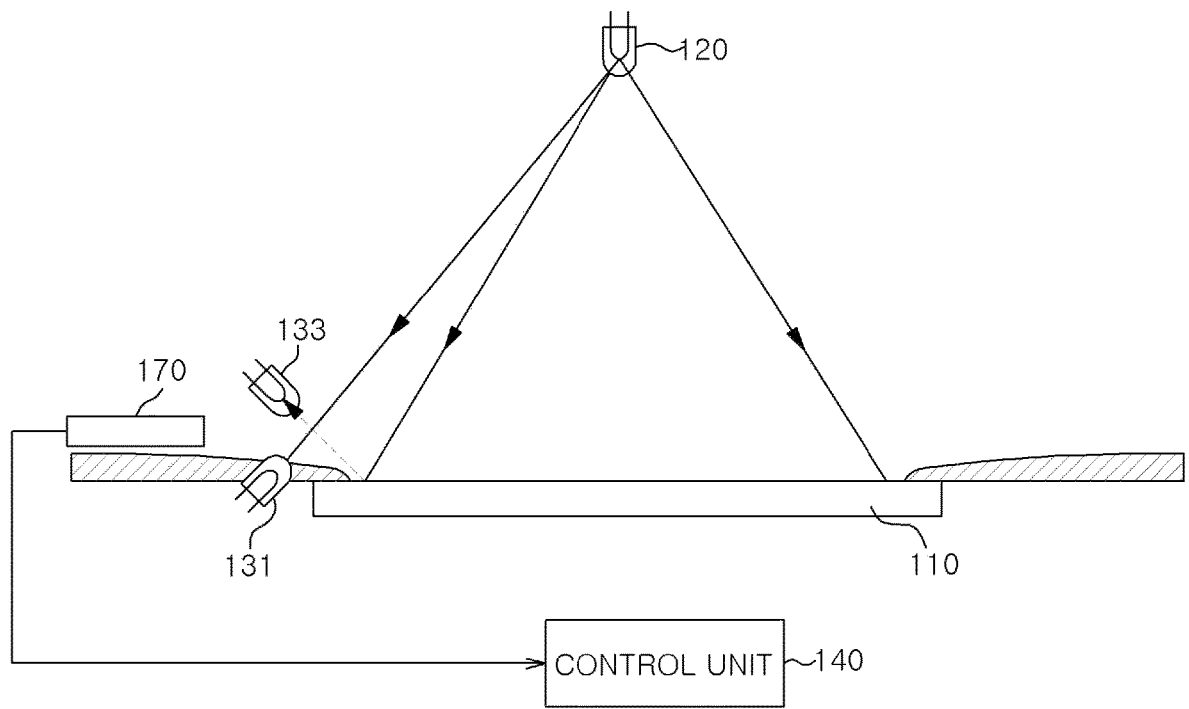
FIG. 3 shows another configuration of an apparatus for sterilizing a fingerprint recognition area according to one embodiment.

FIG. 3 shows another configuration of the apparatus 100 for sterilizing the fingerprint recognition area according to one embodiment.

Referring to FIG. 3, the apparatus 100 for sterilizing the fingerprint recognition area may further include an environmental information measuring sensor 170.

The environmental information measuring sensor 170 may include a temperature sensor or a humidity sensor.

The environmental information measuring sensor 170 may be positioned within a predetermined distance from the sterilizing light emitting unit 120.

In this case, the control unit 140 may reset a predetermined reference energy based on sensed temperature or sensed humidity.

On the other hand, the control unit 140 may adjust output intensity of the sterilizing light of the sterilizing light emitting unit 120 based on the sensed temperature or the sensed humidity. For example, if the temperature sensed by the temperature sensor is higher than a predetermined temperature value or the humidity sensed by the humidity sensor is higher than a predetermined humidity value, the control unit 140 may lower the output intensity of the sterilizing light of the sterilizing light emitting unit 120, but is not limited thereto.

On the other hand, the control unit 140 may control the output intensity of the sterilizing light of the sterilizing light emitting unit 120 according to a duration determined in which the body of the user has been contacted on the finger contact unit 110 for obtaining the fingerprint image, the number of times determined that the body of the user has been contacted, a contamination level, and transparency, and the like, but is not limited thereto.

Figure 4:
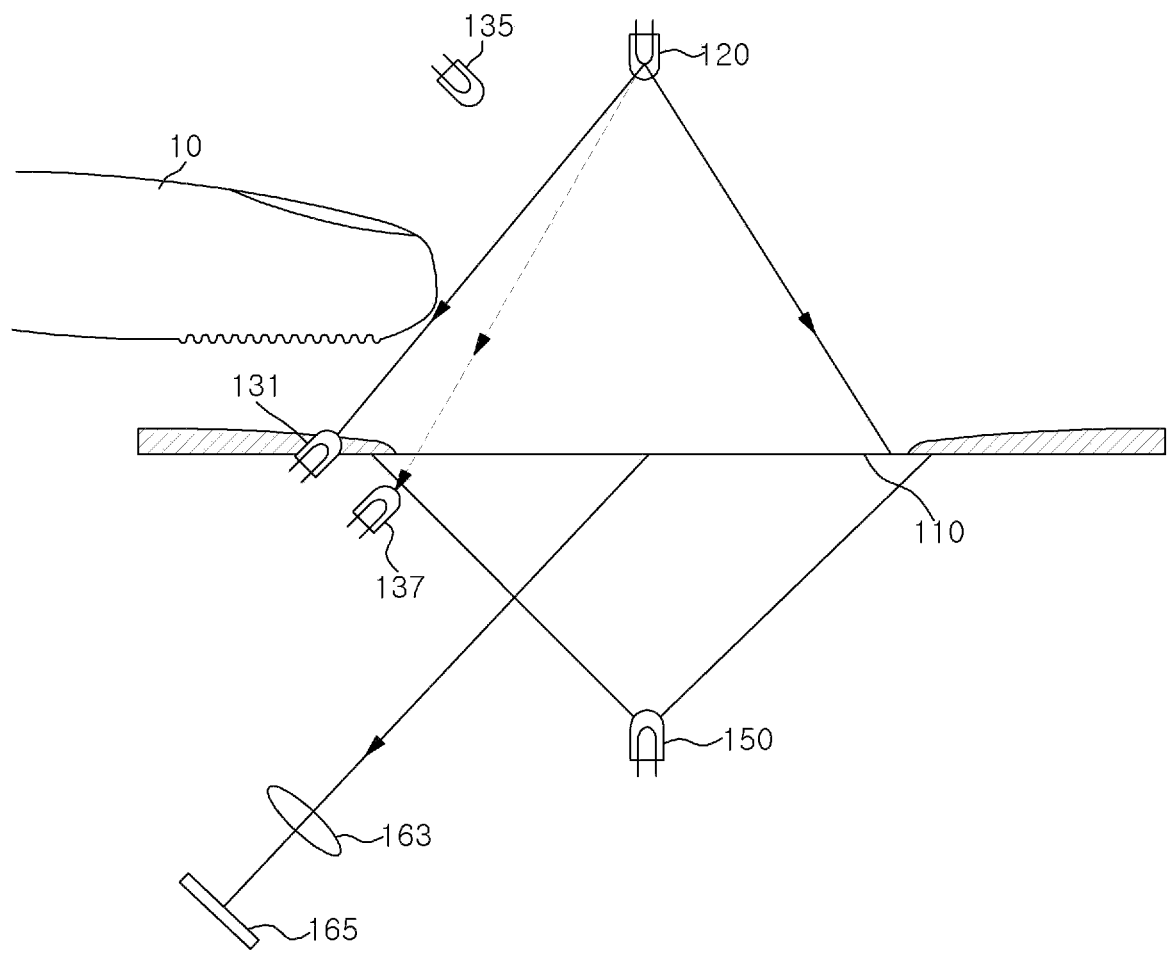
FIG. 4 shows a diagram illustrating a situation before a body of a user contacts a finger contact unit for obtaining a fingerprint image according to one embodiment.

FIG. 4 shows a diagram illustrating a situation before a body 10 of a user contacts the finger contact unit 110 for obtaining the fingerprint image according to one embodiment.

Referring to FIG. 4, before the body of the user 10 (which may be a finger of the user) contacts the finger contact unit 110 for obtaining the fingerprint image (or before the body 10 of the user is inserted onto the finger contact unit 110 for obtaining the fingerprint image), a sterilizing light may be sensed by the first optical sensing unit 131 for sensing a direct light of the sterilizing light emitted from the sterilizing light emitting unit 120 and by the fourth optical sensing unit 137 for sensing a transmitted light that is the sterilizing light emitted from the sterilizing light emitting unit 120 and then transmitted through the finger contact unit 110 for obtaining the fingerprint image.

However, the sterilizing light may not be sensed by the third optical sensing unit 135 for sensing a reflected light that is the sterilizing light emitted from the sterilizing light emitting unit 120 and then reflected by the body 10 of the user (which may be the finger of the user) or an object.

Figure 5:
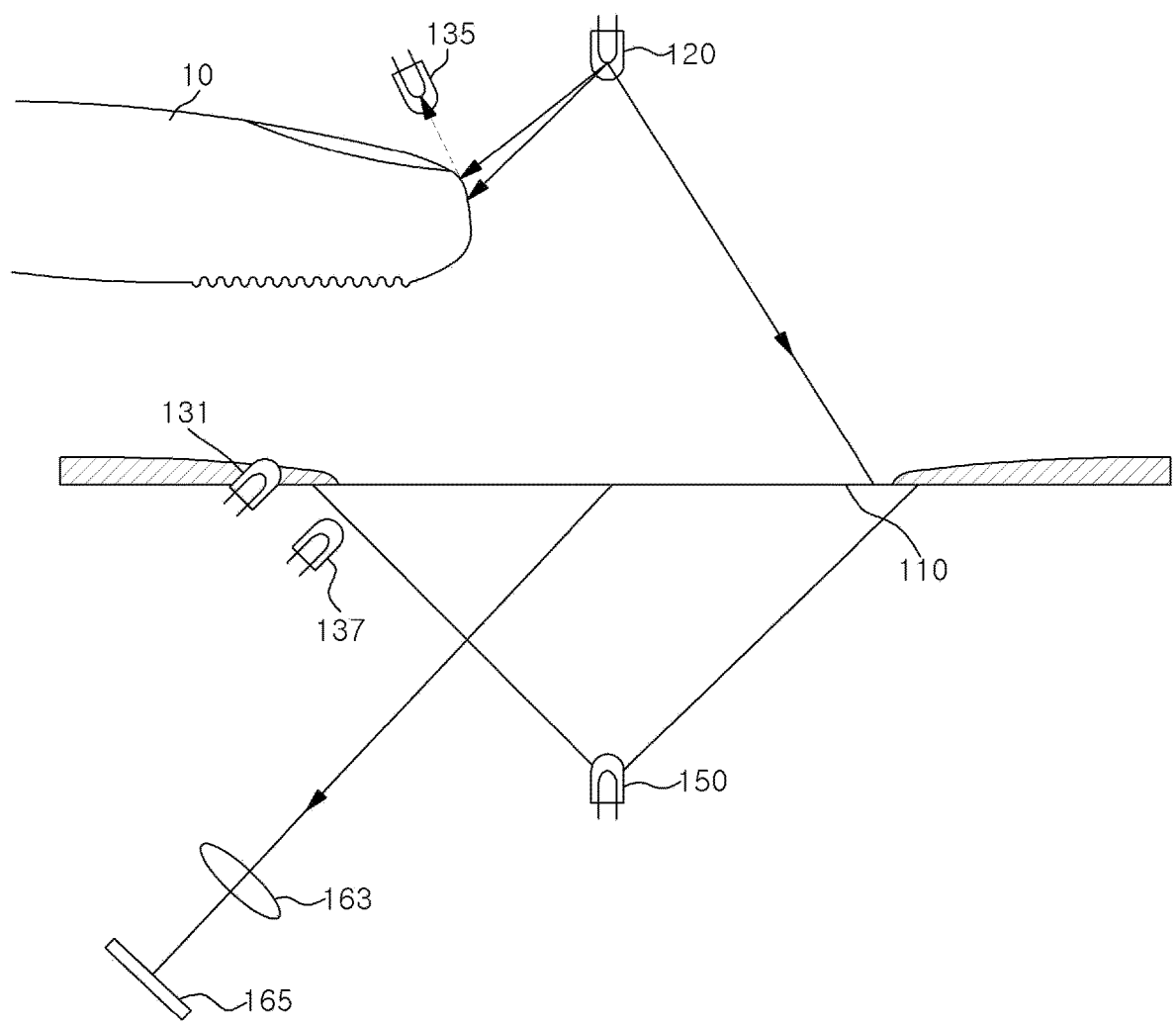
FIG. 5 shows a diagram illustrating a situation when a body of a user contacts a finger contact unit for obtaining a fingerprint image according to one embodiment.

FIG. 5 shows a diagram illustrating a situation when the body 10 of the user contacts the finger contact unit 110 for obtaining the fingerprint image according to one embodiment.

Referring to FIG. 5, when the body 10 of the user (which may be a finger of the user) tries to contact the finger contact unit 110 for obtaining the fingerprint image (or the body of the user is inserted onto the finger contact unit 110 for obtaining the fingerprint image), a sterilizing light may be sensed by the third optical sensing unit 135 for sensing a reflected light that is the sterilizing light emitted from the sterilizing light emitting unit 120 and then reflected by the body 10 of the user (which may be the finger of the user) or an object.

However, the sterilizing light may not be sensed by the first optical sensing unit 131 for sensing a direct light of the sterilizing light emitted from the sterilizing light emitting unit 120 and by the fourth optical sensing unit 137 for sensing a transmitted light that is the sterilizing light emitted from the sterilizing light emitting unit 120 and then transmitted through the finger contact unit 110 for obtaining the fingerprint image.

Figure 6:
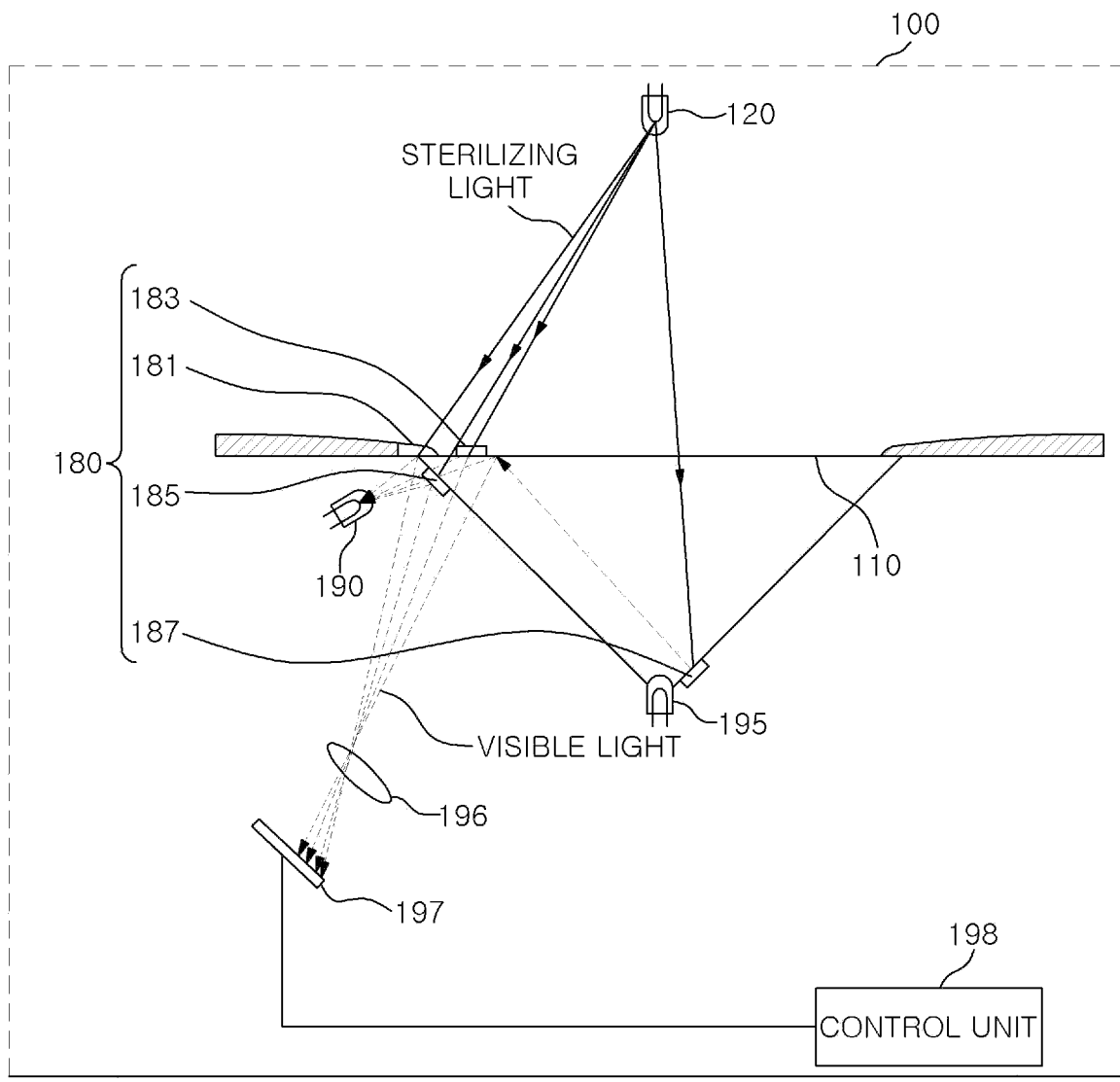
FIG. 6 shows a configuration of an apparatus for sterilizing a fingerprint recognition area according to another embodiment.

FIG. 6 shows a configuration of an apparatus 100 for sterilizing a fingerprint recognition area according to another embodiment.

Referring to FIG. 6, the apparatus 100 for sterilizing the fingerprint recognition area according to another embodiment may include the finger contact unit 110 for obtaining the fingerprint image, the sterilizing light emitting unit 120, an illuminant 180, an optical sensing unit 190, a photographic lighting device 195, a lens 196, an image sensor 197, and a control unit 198, but is not limited thereto.

The finger contact unit 110 for obtaining the fingerprint image and the sterilizing light emitting unit 120 have the same characteristics as those included in the apparatus 100 for sterilizing the fingerprint recognition area according to one embodiment, and thus will not be described separately.

When the sterilizing light having a first wavelength emitted from the sterilizing light emitting unit 120 is emitted to the illuminant 180, the illuminant 180 may generate a reflected light having a second wavelength different from the first wavelength.

Herein, the first wavelength may be in a wavelength range of infrared rays or ultraviolet rays, and the second wavelength may be in a wavelength range of visible light.

The optical sensing unit 190 may be positioned under the finger contact unit 110 for obtaining the fingerprint image, and may sense the reflected light having the second wavelength generated from the illuminant 180 (which may be the visible light).

The photographic lighting device 195 may emit an illumination (or a light) for photographing an image of a body of a user (for example, a finger) contacted on the finger contact unit 110 for obtaining the fingerprint image.

The lens 196 may receive and pass the reflected light having the second wavelength (which may be the visible light) generated when the sterilizing light is reflected by the illuminant 180 to which the sterilizing light emitted by the sterilizing light emitting unit 120 is emitted.

The image sensor 197 may sense the reflected light having the second wavelength transmitted through the lens 196, thereby outputting an electrical signal corresponding to the second wavelength, and transmitting the output electrical signal to a signal circuit unit (not shown). In this case, the signal circuit unit may process the electrical signal transmitted from the image sensor 197 and transmit the processed signal to the control unit 198.

The control unit 198 may calculate energy of the sterilizing light based on the processed signal received from the signal circuit unit, and may determine an OFF timing of the sterilizing light emitting unit 120 based on a comparison between an accumulated value of the energy of the sterilizing light calculated from an ON timing of the sterilizing light emitting unit 120 and a predetermined reference energy.

On the other hand, the photographic lighting device 195, the lens 196, and the image sensor 197 may be replaced with a configuration of a photo (or an image) imaging device (for example, a camera), but are not limited thereto.

Figure 7:
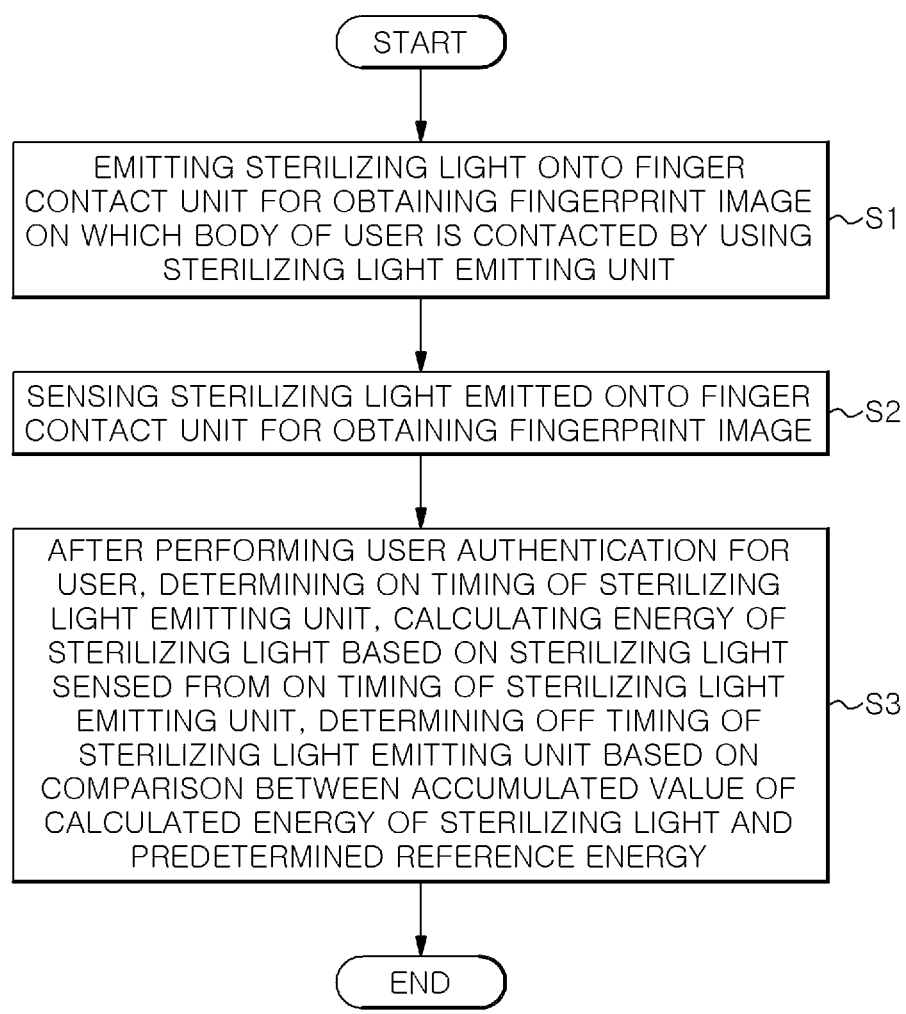
FIG. 7 shows a flowchart illustrating a method of sterilizing a fingerprint recognition area according to one embodiment.

FIG. 7 shows a flowchart illustrating a method of sterilizing a fingerprint recognition area according to one embodiment. The method of sterilizing the fingerprint recognition area illustrated in FIG. 7 may be performed by the apparatus 100 for sterilizing the fingerprint recognition area illustrated in FIG. 1. In addition, the method of sterilizing the fingerprint recognition area illustrated in FIG. 7 may be an example.

Referring to FIG. 7, in a step S1, the sterilizing light emitting unit 120 may emit the sterilizing light onto the finger contact unit 110 for obtaining the fingerprint image on which a body of a user is contacted under control of the control unit 140.

In a step S2, the optical sensing unit 130 may sense the sterilizing light emitted onto the finger contact unit 110 for obtaining the fingerprint image.

In this case, the optical sensing unit 130 may output a current or a voltage corresponding to the sensed sterilizing light.

In a step S3, the control unit 140 may determine an ON timing of the sterilizing light emitting unit 120 after performing user authentication for the user, and may calculate energy of the sterilizing light based on the sterilizing light sensed from the ON timing of the sterilizing light emitting unit 120. The control unit 140 may determine an OFF timing of the sterilizing light emitting unit 120 based on a comparison between an accumulated value of the calculated energy of the sterilizing light and a predetermined reference energy.

As described above, according to one embodiment, the apparatus 100 for sterilizing the fingerprint recognition area may determine the ON timing (which may be the timing to emit the sterilizing light) of the sterilizing light emitting unit 120 after performing the user authentication for the user, and may calculate the energy of the sterilizing light based on the sterilizing light sensed from the ON timing of the sterilizing light emitting unit 120, and may determine the OFF timing (which may be the timing not to emit the sterilizing light) of the sterilizing light emitting unit 120 based on the comparison between the accumulated value of the calculated energy of the sterilizing light and the predetermined reference energy.

In addition, since the predetermined reference energy may be changed according to the duration determined in which the body has been contacted on the finger contact unit 110 for obtaining the fingerprint image, the number of times determined that the body has been contacted, the contamination level, the transparency, the temperature and the humidity, an optimum sterilization effect may be obtained by resetting the reference energy that is determined to have the sterilization effect according to changes in a surrounding environment.

Combinations of steps in the flowcharts of the present disclosure can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the steps of the flowchart.

These computer program instructions may also be stored in a computer usable or computer readable memory that can direct a computer or other programmable data processing apparatuses to function in a particular manner, such that the instructions stored in the computer usable or computer readable medium can produce an article of manufacture including instructions which implement the function specified in the steps of the flowcharts.

The computer program instructions may also be loaded onto a computer or other programmable data processing apparatuses to cause a series of operational steps to be performed on the computer or other programmable apparatuses to produce a computer implemented process such that the instructions which execute on the computer or other programmable apparatuses provide processes for implementing the functions specified in the steps of the flowcharts.

Each step in the flowchart may represent a module, segment, or portion of code, which comprises one or more executable instructions for implementing the specified logical function(s). It should also be noted that, in some alternative implementations, the functions noted in the step may occur out of the order noted in the figures. For example, two steps shown in succession may, in fact, be executed substantially concurrently, or the steps may sometimes be executed in the reverse order, depending upon the functionality involved.

The above description is merely exemplary description of the technical scope of the present disclosure, and it will be understood by those skilled in the art that various changes and modifications can be made without departing from original characteristics of the present disclosure. Therefore, the embodiments disclosed in the present disclosure are intended to explain, not to limit, the technical scope of the present disclosure, and the technical scope of the present disclosure is not limited by the embodiments. The protection scope of the present disclosure should be interpreted based on the following claims and it should be appreciated that all technical scopes included within a range equivalent thereto are included in the protection scope of the present disclosure.

What is claimed is:

1. An apparatus for sterilizing a fingerprint recognition area, the apparatus comprising:
   at least one finger contact unit for obtaining a fingerprint image on which a body of a user is contacted;
   a sterilizing light emitting unit configured to emit the sterilizing light onto the at least one finger contact unit for obtaining the fingerprint image;
   at least one optical sensing unit configured to sense the sterilizing light emitted onto the at least one finger contact unit for obtaining the fingerprint image; and
   a control unit configured to determine an ON timing of the sterilizing light emitting unit after performing user authentication for the user, calculate energy of the sterilizing light based on the sterilizing light sensed by the at least one optical sensing unit from the ON timing of the sterilizing light emitting unit, and determine an OFF timing of the sterilizing light emitting unit based on a result of comparing an accumulated value of the calculated energy of the sterilizing light with a predetermined reference energy,
   wherein the control unit is configured to adjust the predetermined reference energy based on a time during which the body of the user has contacted with the at least one finger contact unit and adjust the predetermined reference energy regardless of a number of times that the body of the user has contacted with the at least one finger contact unit, and
   wherein, when the predetermined reference energy is adjusted to be greater, the control unit redetermines the ON timing and the OFF timing so that a duration between the ON timing and the OFF timing becomes longer.

2. The apparatus of claim 1, further comprising:
   an imaging device configured to capture the fingerprint image of a finger of the user contacted on the at least one finger contact unit for obtaining the fingerprint image,
   wherein the control unit is configured to perform the user authentication based on the fingerprint image of the user captured by the imaging device.

3. The apparatus of claim 1, wherein the at least one optical sensing unit is further configured to output a current or a voltage corresponding to the sensed sterilizing light, and
   wherein the control unit is configured to calculate the energy of the sterilizing light by using the current or the voltage output from the at least one optical sensing unit.

4. The apparatus of claim 3, wherein the control unit is further configured to control the sterilizing emitting unit to be off if the accumulated value of the energy is equal to or greater than the predetermined reference energy.

5. The apparatus of claim 1, wherein the sterilizing light includes infrared rays or ultraviolet rays.

6. The apparatus of claim 1, wherein the predetermined reference energy is adjusted to have the greater value as the time becomes longer.

7. The apparatus of claim 1, wherein the control unit is further configured to adjust the predetermined reference energy based on a calculated contamination level of the at least one finger contact unit for obtaining the fingerprint image.

8. The apparatus of claim 7, wherein the contamination level calculated by the control unit is calculated based on a comparison between a reference image showing the at least one finger contact unit for obtaining the fingerprint image in an initial state in which the body of the user has not been contacted on the at least one finger contact unit for obtaining the fingerprint image and a captured image showing the at least one finger contact unit for obtaining the fingerprint image after the body of the user is inserted into the apparatus for sterilizing the fingerprint recognition area and contacted on the at least one finger contact unit for obtaining the fingerprint image, and after the user authentication is terminated.

9. The apparatus of claim 8, wherein the contamination level calculated by the control unit is calculated based on a change in contrast between the reference image and the captured image.

10. The apparatus of claim 7, wherein the control unit is further configured to obtain an area ratio of the body of the user contacted on the at least one finger contact unit for obtaining the fingerprint image to the at least one finger contact unit for obtaining the fingerprint image in an image showing the at least one finger contact unit for obtaining the fingerprint image in a state in which the body of the user is inserted and contacted on the at least one finger contact unit for obtaining the fingerprint image.

11. The apparatus of claim 1, wherein the control unit is further configured to reset the predetermined reference energy based on calculated transparency of the at least one finger contact unit for obtaining the fingerprint image, and
the transparency is calculated based on a comparison of an amount of a light sensed by an optical sensing unit sensing a direct light of the sterilizing light emitted from the sterilizing light emitting unit to those sensed by an optical sensing unit sensing a transmitted light that the sterilizing light emitted from the sterilizing light emitting unit is transmitted through the at least one finger contact unit for obtaining the fingerprint image.

12. The apparatus of claim 1, further comprising a temperature sensor or a humidity sensor,
wherein the control unit is further configured to reset the predetermined reference energy based on sensed temperature and sensed humidity.

13. The apparatus of claim 1, further comprising a temperature sensor or a humidity sensor,
wherein the control unit is further configured to adjust output intensity of the sterilizing light emitting unit based on sensed temperature and sensed humidity.

14. The apparatus of claim 1, wherein the control unit is further configured to determine that the sterilizing light emitting unit is deteriorated if the sterilizing light sensed through the at least one optical sensing unit is out of a predetermined intensity range of the sterilizing light.

15. The apparatus of claim 14, wherein the control unit is further configured to output information including a message indicating that an abnormality has occurred in the sterilizing light emitting unit if the control unit determines that the sterilizing light emitting unit is deteriorated.

16. The apparatus of claim 1, further comprising:
at least one illuminant configured to generate, if a sterilizing light having a first wavelength is emitted from the sterilizing light emitting unit onto the at least one illuminant, a reflected light having a second wavelength different from the first wavelength,
wherein the first wavelength is in a wavelength range of infrared rays or ultraviolet rays, and
the second wavelength is in a wavelength range of visible light.

17. The apparatus of claim 16, further comprising:
an optical sensing unit, positioned under the at least one finger contact unit for obtaining the fingerprint image, configured to sense the reflected light having the second wavelength generated from the at least one illuminant.

18. The apparatus of claim 17, further comprising:
an imaging sensor configured to output an electrical signal corresponding to the second wavelength by sensing the reflected light generated from the at least one illuminant.

19. A method of sterilizing a fingerprint recognition area performed by an apparatus for sterilizing the fingerprint recognition area, the method comprising:
emitting a sterilizing light onto at least one finger contact unit for obtaining a fingerprint image on which a body of a user is contacted by using a sterilizing light emitting unit;
sensing the sterilizing light emitted onto the at least one finger contact unit for obtaining the fingerprint image; and
determining an ON timing of the sterilizing light emitting unit after performing user authentication for the user, calculating energy of the sterilizing light based on the sensed sterilizing light from the ON timing of the sterilizing light emitting unit, and determining an OFF timing of the sterilizing light emitting unit based on a result of comparing an accumulated value of the calculated energy of the sterilizing light with a predetermined reference energy,
wherein the predetermined reference energy is adjusted based on a time during which the body of the user contacts with the at least one finger contact unit and the predetermined reference energy is adjusted regardless of a number of times that the body of the user has contacted with the at least one finger contact unit, and
wherein, when the predetermined reference energy is adjusted to be greater, the control unit redetermines the ON timing and the OFF timing so that a duration between the ON timing and the OFF timing becomes longer.

20. An apparatus for sterilizing a fingerprint recognition area, the apparatus comprising:
at least one finger contact unit for obtaining a fingerprint image on which a body of a user is contacted;
a sterilizing light emitting unit configured to emit the sterilizing light onto the at least one finger contact unit for obtaining the fingerprint image;
at least one optical sensing unit configured to sense the sterilizing light emitted onto the at least one finger contact unit for obtaining the fingerprint image; and
a control unit configured to determine an ON timing of the sterilizing light emitting unit after performing user authentication for the user, calculate energy of the sterilizing light based on the sterilizing light sensed by the at least one optical sensing unit from the ON timing of the sterilizing light emitting unit, and determine an OFF timing of the sterilizing light emitting unit based on a result of comparing an accumulated value of the calculated energy of the sterilizing light with a predetermined reference energy,
wherein the at least one optical sensing unit comprises:
a first optical sensing unit configured to sense a direct light emitted from the sterilizing light emitting unit;
a second optical sensing unit configured to sense a first reflected light that the sterilizing light, which is emitted from the sterilizing light emitting unit, is reflected by the at least one finger contact unit for obtaining the fingerprint image;
a third optical sensing unit configured to sense a second reflected light that the sterilizing light, which is emitted from the sterilizing light emitting unit, is reflected by the body of the user or an object; and
a fourth optical sensing unit configured to sense a transmitted light that the sterilizing light, which is emitted from the sterilizing light emitting unit, is transmitted through the at least one finger contact unit for obtaining the fingerprint image.

21. The apparatus of claim 20, wherein the control unit is further configured to:
- determine a start time at which a first sensing state in which at least one of the direct light, the first reflected light, and the transmitted light is not sensed by the first optical sensing unit, the second optical sensing unit, and the fourth optical sensing unit respectively or the second reflected light is sensed by the third optical sensing unit changes to a second sensing state in which the direct light, the first reflected light, and the transmitted light are sensed by the first optical sensing unit, the second optical sensing unit, and the fourth optical sensing unit respectively or the second reflected light is not sensed by the third optical sensing unit; and
- determine an end time, after determining the start time, at which the second sensing state changes to the first sensing state,
- wherein the control unit is configured to adjust the predetermined reference energy based on a time during which the body of the user has contacted with the at least one finger contact unit
- wherein the time is determined based on the start time and the end time.

\* \* \* \* \*